US00PP37549P2

(12) United States Plant Patent
Roper

(10) Patent No.: US PP37,549 P2
(45) Date of Patent: Aug. 4, 2026

(54) ALMOND TREE NAMED 'Mary Jane'

(50) Latin Name: *Prunis dulcis*
Varietal Denomination: Mary Jane

(71) Applicant: Utah State University, Logan, UT (US)

(72) Inventor: Teryl Roper, Newton, MA (US)

(73) Assignee: Utah State University, Logan, UT (US)

( * ) Notice: Subject to any disclaimer, the term of this patent is extended or adjusted under 35 U.S.C. 154(b) by 0 days.

(21) Appl. No.: 19/056,182

(22) Filed: Feb. 18, 2025

(51) Int. Cl.
*A01H 5/10* (2018.01)
*A01H 5/00* (2018.01)
*A01H 6/74* (2018.01)

(52) U.S. Cl.
USPC ..... Plt./155
CPC ..... *A01H 6/7427* (2018.05); *A01H 5/00* (2013.01)

(58) Field of Classification Search
USPC ..... Plt./155
CPC ..... A01H 6/7427; A01H 5/10
See application file for complete search history.

*Primary Examiner* — Keith O. Robinson
(74) *Attorney, Agent, or Firm* — G. Harley Blosser; Sandberg Phoenix & von Gontard, PC

(57) ABSTRACT

A new and distinct cultivar of almond tree (*Prunus dulcis*) designated as 'Mary Jane' originated from seed collected in Tashkent Province, Uzbekistan, and was developed through evaluation at Utah State University. The cultivar is characterized by uniform soft-shelled nuts averaging 2.1 grams in shell with 1.2-gram sweet kernels, white flowers with reddish centers, late September maturity, and successful propagation through greenhouse facilities in Richmond, Utah.

5 Drawing Sheets

Current name or designation: [The Mary Jane Almond Tree (*Prunus dulcis*)] 'MARY JANE'.

GENERAL STATEMENTS

The information below relates to a new and distinct variety/cultivar of almond tree (*Prunus dulcis*).

Development: The Mary Jane Almond Tree (*Prunus dulcis*) was developed by Utah State University through systematic germplasm collection initiatives. The cultivar's genetic material originates from a seed collected in Tashkent Province, Uzbekistan of unknown parentage (not patented). Following procurement through official plant import permits, the genetic material underwent greenhouse propagation at facilities in Richmond, Utah. The cultivar's development proceeded through field evaluations at the Peterson family agricultural operation in Thatcher, Box Elder County, Utah, where the initial trial orchard was established.

Propagation: Asexual reproduction of this new and distinct variety of almond tree has been accomplished through grafting and budding techniques onto both peach and almond rootstocks. Initial propagation trials were conducted at the Utah State University research facilities in Richmond, Utah. The compatibility with multiple understocks provides flexibility in cultivation, allowing growers to select appropriate rootstock based on local soil conditions and climate factors. Subsequent evaluations of these asexually reproduced specimens have demonstrated that the asexual reproductions maintain fidelity to the original tree. All characteristics of the original specimen appear to be transmitted through succeeding asexual propagations, ensuring consistent trait expression across propagated specimens.

Uniqueness: The 'Mary Jane' Almond (*Prunus dulcis*) exhibits morphological and agronomic characteristics that, in combination, distinguish it from existing cultivars. As its parentage is unknown (unpatented), the 'Mary Jane' Almond Tree is compared herein to a related type/variety of almond tree, named the 'Bennett-Hickman' (U.S. Plant Pat. No. 26,083 P3), also of unknown parentage. Compared to the 'Bennett-Hickman' and other almond trees, the 'Mary Jane' almond tree produces uniformly soft-shelled nuts with an average in-shell weight of 2.1 grams, containing kernels that consistently measure approximately 1.2 grams. The floral display consists of white petals with reddish centers, contributing significantly to the tree's ornamental value. The soft shell characteristic allows for easy kernel extraction without tools, while maintaining favorable kernel-to-shell ratios across harvests. This combination of nut size, shell texture, and late September maturation timing creates a unique cultivar profile particularly suited to home garden settings.

PRODUCTION AND HARVESTING

The 'Mary Jane' Almond requires standard orchard cultivation practices, with emphasis on full sun exposure and well-drained soil conditions. The cultivar exhibits obligate cross-pollination requirements, being non-self-fruitful and necessitating appropriate pollinizer cultivars for commercial production. Site selection should prioritize areas with adequate soil drainage and exposure to facilitate optimal tree health and nut development. Cultural practices typical of commercial almond production are suitable for this cultivar, with timing of operations determined by its specific bloom-to-harvest interval.

PHOTOGRAPHS ACCOMPANYING SUBMISSION

The photographs submitted herewith show the color of our new variety/cultivar as nearly as reasonably possible to make the same in a color illustration of this character (with reference to The Royal Horticultural Society, (London) Colour Chart, aka the "R.H.S.C.C." herein):

DESCRIPTION OF THE NEW CULTIVAR

Figure 1:
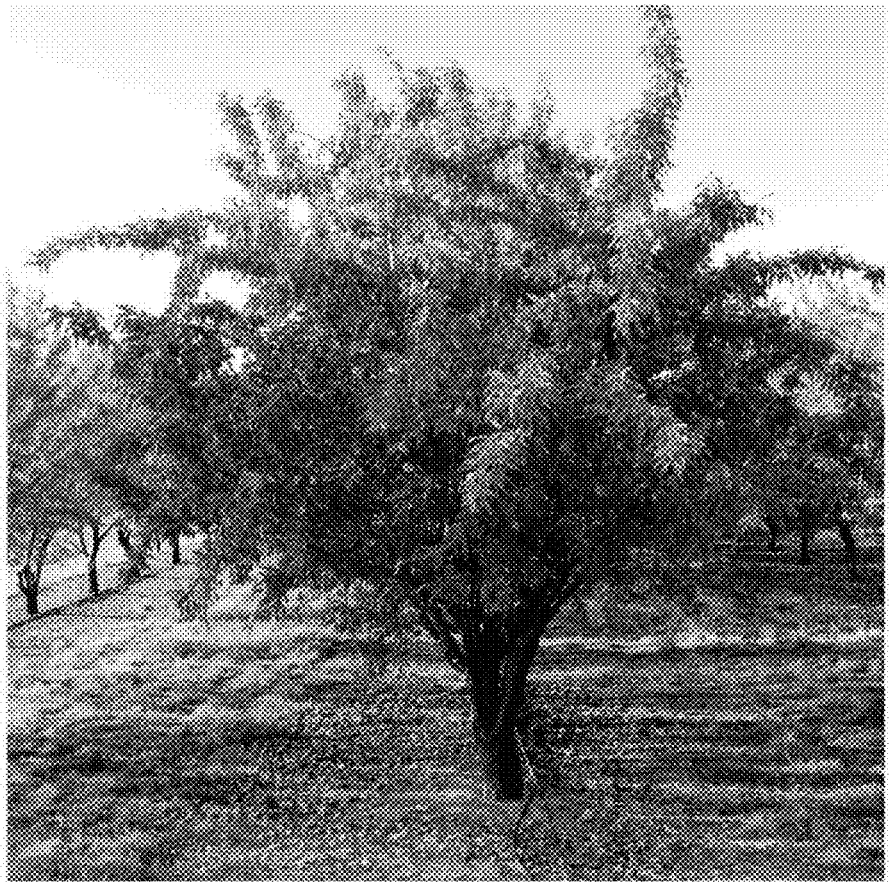
FIG. 1 is a photograph of an estimated 10-year old specimen of the new and distinct variety almond tree 'Mary Jane'.
Figure 2:
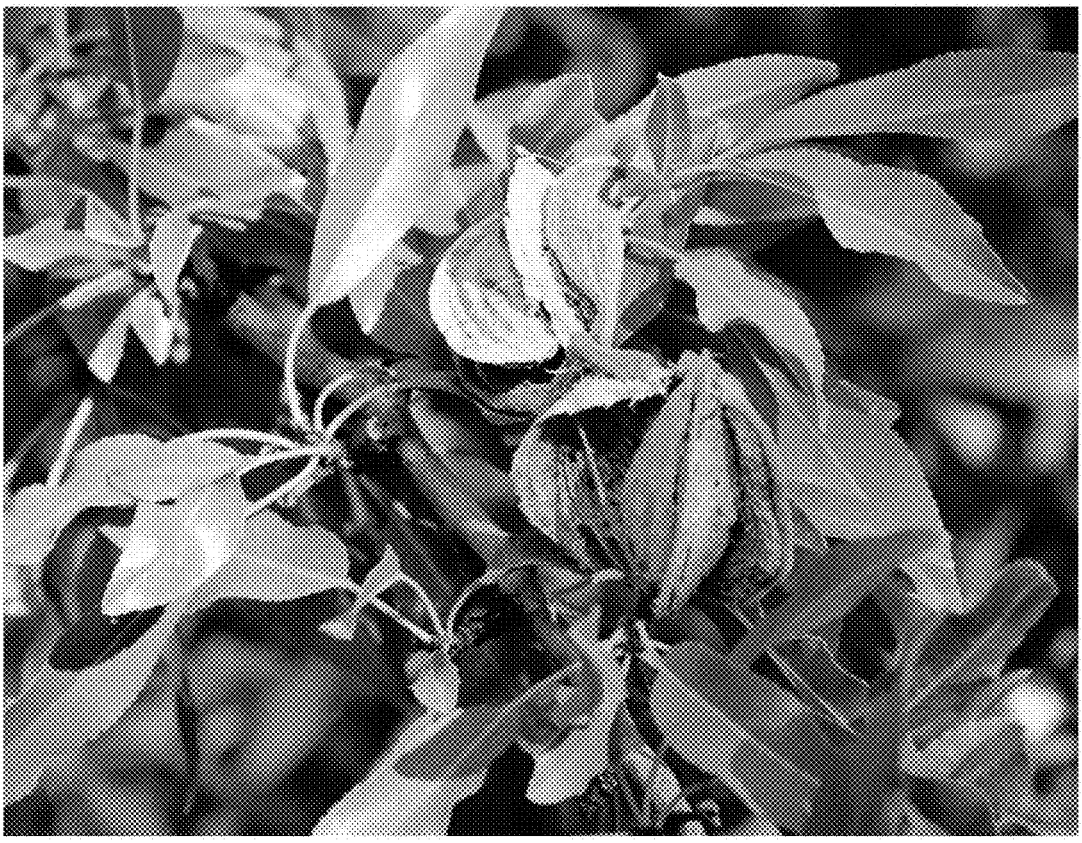
FIG. 2 is a photograph of the closed blossoms of the tree.
Figure 3:
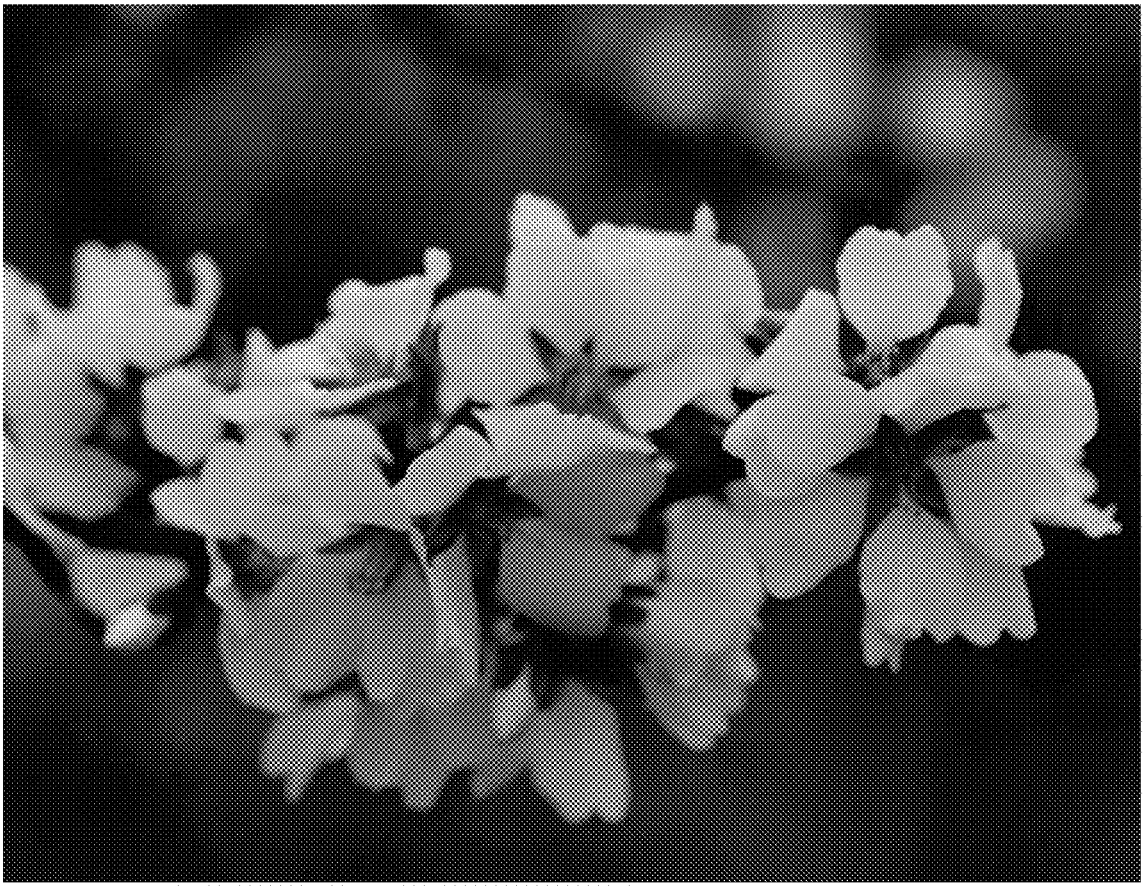
FIG. 3 is a photograph of the open blossoms of the tree.
Figure 4:
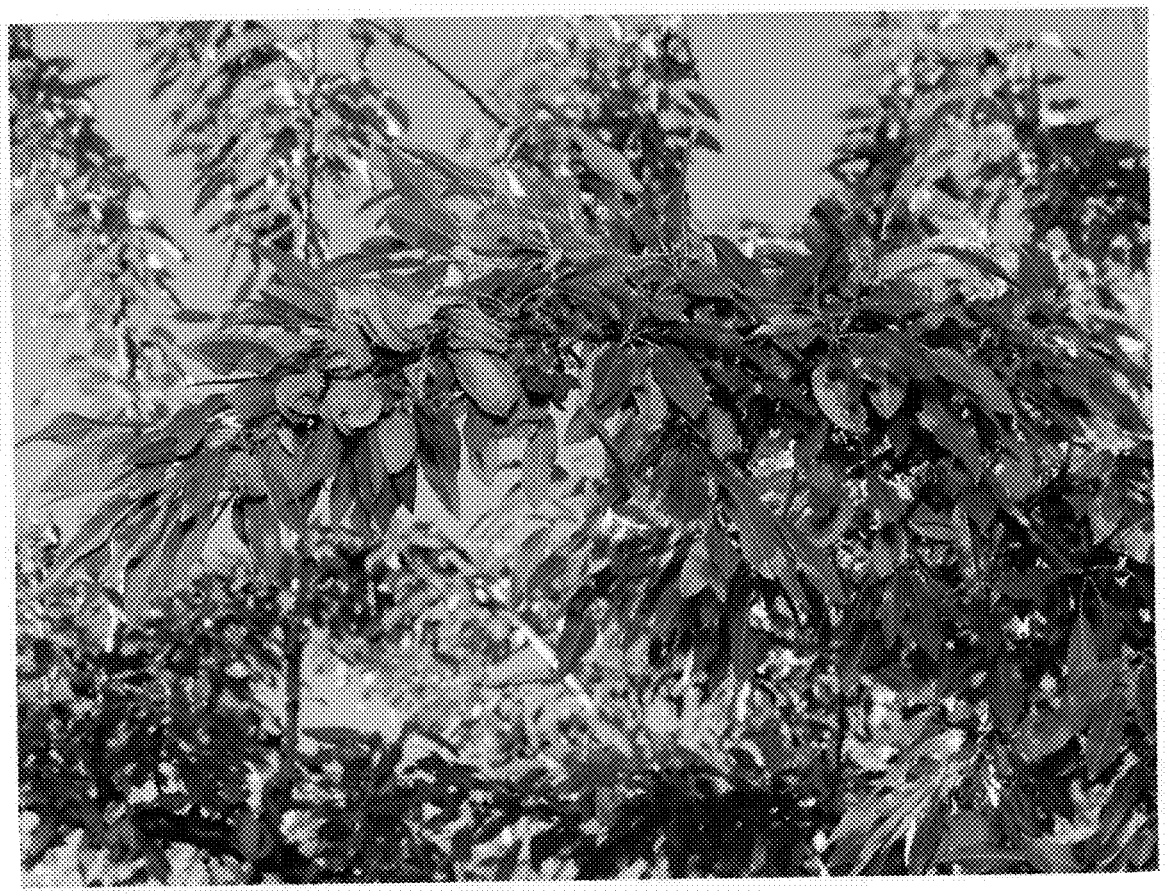
FIG. 4 is a photograph of the limb and blossom habit of the tree.
Figure 5:
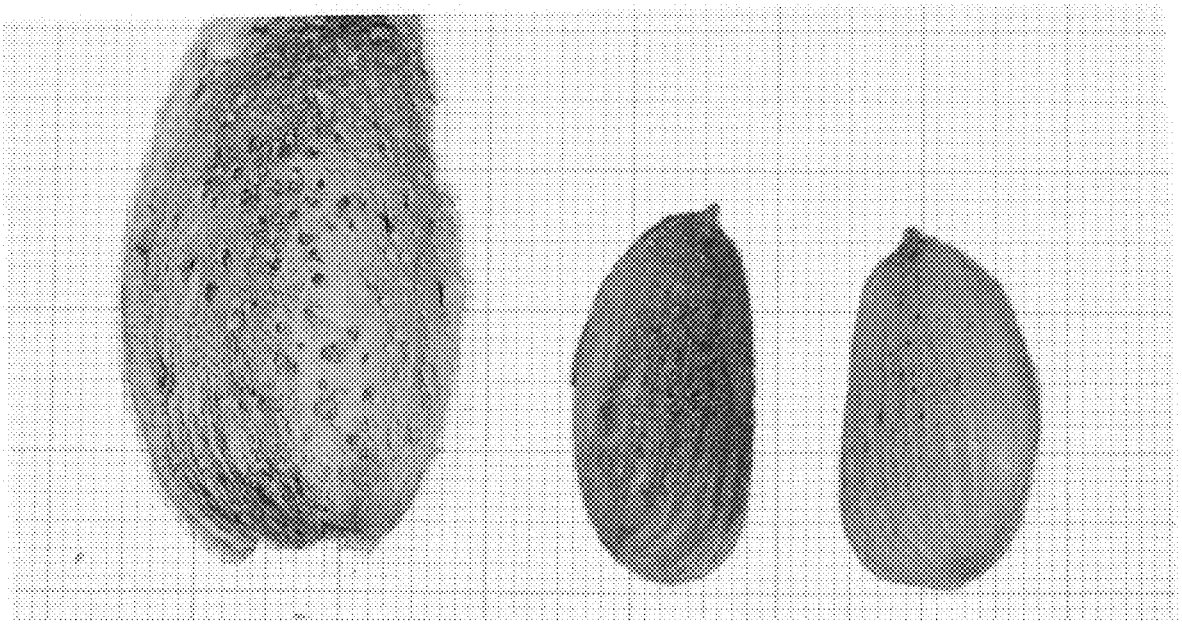
FIG. 5 is a photograph of the almond of the tree.

The following is a detailed description of our new cultivar of almond tree 'Mary Jane'.

Other than as set forth below, as of this time, no other characteristics of our new almond tree 'Mary Jane' have been observed by the inventors which are substantially different from the characteristics common to almond trees.

Classification:

*Family*.—Rosaceae.

*Botanical*.—*Prunus amygdalus*.

*Common*.—Almond.

*Denomination*.—Batsch.

General description:

*Plant type*.—Nut tree.

*Propagation type*.—Asexual via grafting or budding. Peach and almond are compatible understocks.

*Height from soil level to top of foliage*.—5.5-6.5 meters, allowing for rootstock effect.

*Plant spread*.—4-5 meters, depending on adjacent plants.

*Number of basal shoots per plant*.—One.

*Growth rate*.—Typically ranges from 8 to 10 inches, especially as a young tree.

*Propagation type*.—Asexual via budding or grafting.

*Time to initiate rooting*.—Does not root from cuttings.

*Time to develop roots*.—Does not root from cuttings.

*Time to produce a finished plant from a rooted cutting*.—N/A.

*Roots habitat and description*.—Preferably loamy and well drained.

Stem/trunk:

*Length*.—1 meter.

*Diameter*.—30 cm.

*Shape*.—Rounding canopy.

*Color*.—Trunk is reddish brown (RHSCC 178-A).

*Texture*.—Smooth, becoming corky with age.

*Strength*.—Typical for almond.

*Lenticels present*?.—Yes.

*Lenticel length*.—Unknown.

*Lenticel diameter*.—Unknown.

*Lenticel density*.—Unknown.

*Lenticel color*.—Gray.

Branches:

*Diameter*.—Several inches to 8-12 inches is typical.

*Color*.—Reddish brown (RHSCC 178-A).

Foliage description:

*Approximate no. of leaves per plant*.—Thousands to tens of thousands.

*Arrangement*.—Spiral.

*Length*.—8-13 cm.

*Width*.—3.5 cm at midpoint.

*Shape, general*.—Linear.

*Shape of apex*.—Acute.

*Shape of base*.—Acute.

*Margin*.—Serrulate.

*Upper surface texture*.—Smooth.

*Lower surface texture*.—Smooth pand mature foliage is dusty green (RHSCC 197-B). Fall foliage is yellow (RHSCC 15-A).

*Cataphyll*.—None.

Inflorescence: Monopetal. Flowers and fruit are borne on long spurs. Petals are white with reddish centers and are typical for *Prunus* species. Not self-pollinating. Flowering is with or slightly earlier than fellow *Prunus* peach trees grown adjacent. Flowering is with or slightly earlier than peach grown adjacent.

Disease and pest tolerance: The 'Mary Jane' almond is susceptible to common pests and disease typical for almond trees, some of which include crown gall (*Agrobacterium tumefaciens*), white prunicola scale (*Pseudaulacaspis prunicola*), the Fruit-tree leafroller (*Archips argyrospila*), blossom blight fungus (primarily *Monilinia fruticola*), tree mites (*Aculus fockeul*), and shothole fungus (*Wilsonomyces carpophilus*).

Fruit and seed set: Tree requires cross pollination. Tree produces large nuts with sweet kernels and paper shells. Nuts are large with soft shells with a mean weight in 2021 of 2.1 grams in the shell. Kernels averaged 1.2 g. 2021 yield was 5.69 kg/tree with total kernel weight of 2.47 kg/tree. Nuts mature in late September to early October in Northern Utah. The soft shell has a prominent wing. Nuts are prone to double kernels. Kernels are smooth, medium brown, and asymmetrically shaped.

Drought tolerance: Typical for almond and depends in part on rootstock with 1 inch in range of every 10 days anticipated.

Taste: Sweet.

Aroma: Nutty, creamy.

Characteristics of the plant in winter dormancy: In northern Utah, leaf drop occurs in October. The tree is hardy to USDA hardiness zone 6b. Spring flowering is similar in timing to peaches.

I claim:

1. A new and distinct variety of almond tree named 'Mary Jane', as described and illustrated herein.

* * * * *